United States Patent
Sokulin et al.

(10) Patent No.: US 10,206,651 B2
(45) Date of Patent: Feb. 19, 2019

(54) METHODS AND SYSTEMS FOR MEASURING CARDIAC OUTPUT

(71) Applicant: General Electric Company, Schenectady, NY (US)

(72) Inventors: Alexander Sokulin, Tirat Carmel (IL); Menachem Halmann, Wauwatosa, WI (US); Peter Lysyansky, Tirat Carmel (IL); Arcady Kempinski, Tirat Carmel (IL); Lilach Vanuk, Tirat Carmel (IL); Cynthia A. Owen, Powhatan, AR (US)

(73) Assignee: General Electric Company, Schenectady, NY (US)

( * ) Notice: Subject to any disclaimer, the term of this patent is extended or adjusted under 35 U.S.C. 154(b) by 647 days.

(21) Appl. No.: 14/871,052

(22) Filed: Sep. 30, 2015

(65) Prior Publication Data
US 2017/0086780 A1 Mar. 30, 2017

(51) Int. Cl.
*A61B 8/00* (2006.01)
*A61B 8/06* (2006.01)
(Continued)

(52) U.S. Cl.
CPC ........... *A61B 8/065* (2013.01); *A61B 8/02* (2013.01); *A61B 8/4444* (2013.01); *A61B 8/463* (2013.01);
(Continued)

(58) Field of Classification Search
CPC ......... A61B 8/065; A61B 8/02; A61B 8/4444; A61B 8/463; A61B 8/469; A61B 8/488; A61B 8/5207; A61B 8/5223
See application file for complete search history.

(56) References Cited

U.S. PATENT DOCUMENTS

| 4,509,526 A | 4/1985 | Barnes et al. |
| 5,052,395 A | 10/1991 | Burton et al. |

(Continued)

FOREIGN PATENT DOCUMENTS

| WO | 2004051310 A1 | 6/2004 |
| WO | 2006096915 A1 | 9/2006 |
| WO | 2014107769 A1 | 7/2014 |

OTHER PUBLICATIONS

Dr. James Thomas et.al., "Automated Cardiac Output Measurement by Spatiotemporal Integration of Color Doppler Data", circ.ahajournals.org, Jun. 1, 2015, p. 1-12.

(Continued)

*Primary Examiner* — Tse W Chen
*Assistant Examiner* — Joanne M Hoffman
(74) *Attorney, Agent, or Firm* — Dean D. Small; The Small Patent Law Group, LLC

(57) ABSTRACT

Systems and methods for measuring cardiac output are provided. The systems and methods generate an ultrasound image based on ultrasound imaging data of a patient acquired by an ultrasound probe. The systems and methods automatically designate a region of interest (ROI) within the ultrasound image, and acquire spectral data sets for corresponding candidate Doppler gates within the ROI based on Doppler data acquired by the ultrasound probe. The systems and methods automatically identify a select Doppler gate from the candidate Doppler gates based on a characteristic of the spectral data sets, and calculate a cardiac output of the patient based on the select Doppler gate.

23 Claims, 11 Drawing Sheets

(51) Int. Cl.
*A61B 8/02* (2006.01)
*A61B 8/08* (2006.01)
*G06F 19/00* (2018.01)

(52) U.S. Cl.
CPC .............. *A61B 8/469* (2013.01); *A61B 8/488* (2013.01); *A61B 8/5207* (2013.01); *A61B 8/5223* (2013.01); *G06F 19/00* (2013.01); *A61B 8/0883* (2013.01); *A61B 8/5292* (2013.01)

(56) References Cited

U.S. PATENT DOCUMENTS

| | | | | |
|---|---|---|---|---|
| 5,365,929 | A * | 11/1994 | Peterson | A61B 8/06 128/916 |
| 5,501,223 | A * | 3/1996 | Washburn | G01S 7/52085 600/455 |
| 5,690,111 | A | 11/1997 | Tsujino | |
| 6,071,242 | A * | 6/2000 | Lin | A61B 8/06 600/456 |
| 6,221,020 | B1 * | 4/2001 | Lysyansky | A61B 8/06 600/453 |
| 6,390,984 | B1 * | 5/2002 | Pan | A61B 8/06 600/453 |
| 9,060,669 | B1 * | 6/2015 | Mo | A61B 8/565 |
| 9,814,447 | B2 * | 11/2017 | Nakaya | A61B 8/5246 |
| 2002/0173721 | A1 * | 11/2002 | Grunwald | A61B 8/00 600/437 |
| 2003/0013959 | A1 * | 1/2003 | Grunwald | A61B 8/08 600/437 |
| 2004/0068188 | A1 * | 4/2004 | Robinson | G01S 7/52028 600/447 |
| 2005/0004461 | A1 * | 1/2005 | Abend | G01S 7/52026 600/437 |
| 2006/0079782 | A1 * | 4/2006 | Beach | A61B 5/02007 600/450 |
| 2007/0038086 | A1 * | 2/2007 | Ohtsuka | A61B 8/06 600/437 |
| 2007/0083099 | A1 * | 4/2007 | Henderson | A61B 5/02007 600/407 |
| 2009/0069859 | A1 * | 3/2009 | Whinnett | A61B 5/02241 607/30 |
| 2010/0286522 | A1 * | 11/2010 | Beach | A61B 5/02007 600/441 |
| 2010/0331693 | A1 * | 12/2010 | Matsunaga | A61B 8/02 600/443 |
| 2011/0208056 | A1 * | 8/2011 | Datta | A61B 8/06 600/441 |
| 2011/0230764 | A1 * | 9/2011 | Baba | A61B 8/06 600/454 |
| 2012/0215110 | A1 * | 8/2012 | Wilkening | A61B 8/488 600/453 |
| 2013/0006111 | A1 * | 1/2013 | Sasaki | A61B 8/0891 600/441 |
| 2013/0144166 | A1 * | 6/2013 | Specht | G01S 15/8913 600/441 |
| 2014/0018680 | A1 * | 1/2014 | Guracar | A61B 8/463 600/440 |
| 2014/0276072 | A1 * | 9/2014 | Martins | A61B 8/488 600/454 |
| 2014/0336510 | A1 * | 11/2014 | Park | A61B 8/5269 600/441 |
| 2015/0216509 | A1 * | 8/2015 | Yamagata | A61B 8/08 600/443 |
| 2015/0327838 | A1 * | 11/2015 | Francis | A61B 8/0883 600/450 |
| 2016/0310110 | A1 * | 10/2016 | Dodd | A61B 8/54 |

OTHER PUBLICATIONS

Keil Matthias et al, "Combining B-mode and color flow vessel segmentation for registration of hepatic CT and ultrasound volumes", Fraunhofer, Sep. 28, 2012.
International Search Report and Written Opinion for corresponding PCT application No. PCT/US2016/050526 dated Jan. 11, 2017; 11 pages.

* cited by examiner

METHODS AND SYSTEMS FOR MEASURING CARDIAC OUTPUT

FIELD

Embodiments described herein generally relate to measuring cardiac output using a diagnostic medical imaging system.

BACKGROUND OF THE INVENTION

Cardiac output is conventionally used to gauge heart function of a patient. Cardiac output corresponds to an amount of blood pumped out by the heart over time (e.g., a minute), and may be calculated from a heart rate and stroke volume of a patient. Conventionally, ultrasound imaging systems are used as a non-invasive method to evaluate and/or measure blood flow in the heart, typically using Doppler techniques, such as pulsed wave (PW) Doppler.

However, these Doppler techniques are manually intensive and requires the user to have a high technical expertise. For example, the user acquires an ultrasound image of the heart, such as a five chamber view, and will continually position and reposition a PW cursor corresponding to a PW gate until an acceptable flow spectrum is acquired at the PW gate positioned by the user. When an acceptable flow spectrum is acquired, the user will proceed to take measurements from the flow spectrum to calculate the cardiac output. For example, the user will select a velocity time integral (VTI) measurement from a diagnostic list and manually trace the flow spectrum to calculate the VTI. The accuracy and speed of the measurements relies on the expertise of the user, which may limit critical care needs of patients in emergency situations in determining treatments plans.

For these and other reasons, an improved method and system for measuring cardiac output is needed.

BRIEF DESCRIPTION OF THE INVENTION

In one embodiment, a method for measuring cardiac output is provided. The method may include generating an ultrasound image based on ultrasound imaging data of a patient acquired by an ultrasound probe. The method may also include automatically designate a region of interest (ROI) within the ultrasound image, and acquiring spectral data sets for corresponding candidate Doppler gates within the ROI based on Doppler data acquired by the ultrasound probe. The method may further include automatically identifying a select Doppler gate from the candidate Doppler gates based on a characteristic of the spectral data sets, and calculating a cardiac output of the patient based on the select Doppler gate.

In another embodiment, an ultrasound imaging system is provided. The ultrasound imaging system may include an ultrasound probe configured to acquire ultrasound imaging data and Doppler data of a patient. The ultrasound imaging system may also include a memory configured to store programmed instructions, and one or more processors configured to execute the programmed instructions stored in the memory. The one or more processors when executing the programmed instructions perform one or more operations. The one or more processors may generate an ultrasound image system from the ultrasound imaging data, designate a region of interest (ROI) within the ultrasound image, acquire spectral data sets for corresponding candidate Doppler gates within the ROI based on the Doppler data, identify a select Doppler gate from the candidate Doppler gates based on a characteristic of the spectral data sets, and calculate a cardiac output of the patient based on the select Doppler gate.

In another embodiment, a tangible and non-transitory computer readable medium may include one or more computer software modules configured to direct one or more processors. The one or more computer software modules may be configured to direct the one or more processors to generate an ultrasound image based on ultrasound imaging data the patient acquired by ultrasound probe, automatically designate a region of interest (ROI) within the ultrasound image, acquire spectral data sets for corresponding Doppler gates within the ROI based on Doppler data acquired by the ultrasound probe, automatically identify a select Doppler gate from the candidate Doppler gates based on a characteristic of the spectral data sets, and calculate a cardiac output of the patient based on the select Doppler gate.

DETAILED DESCRIPTION OF THE INVENTION

Figure 1:
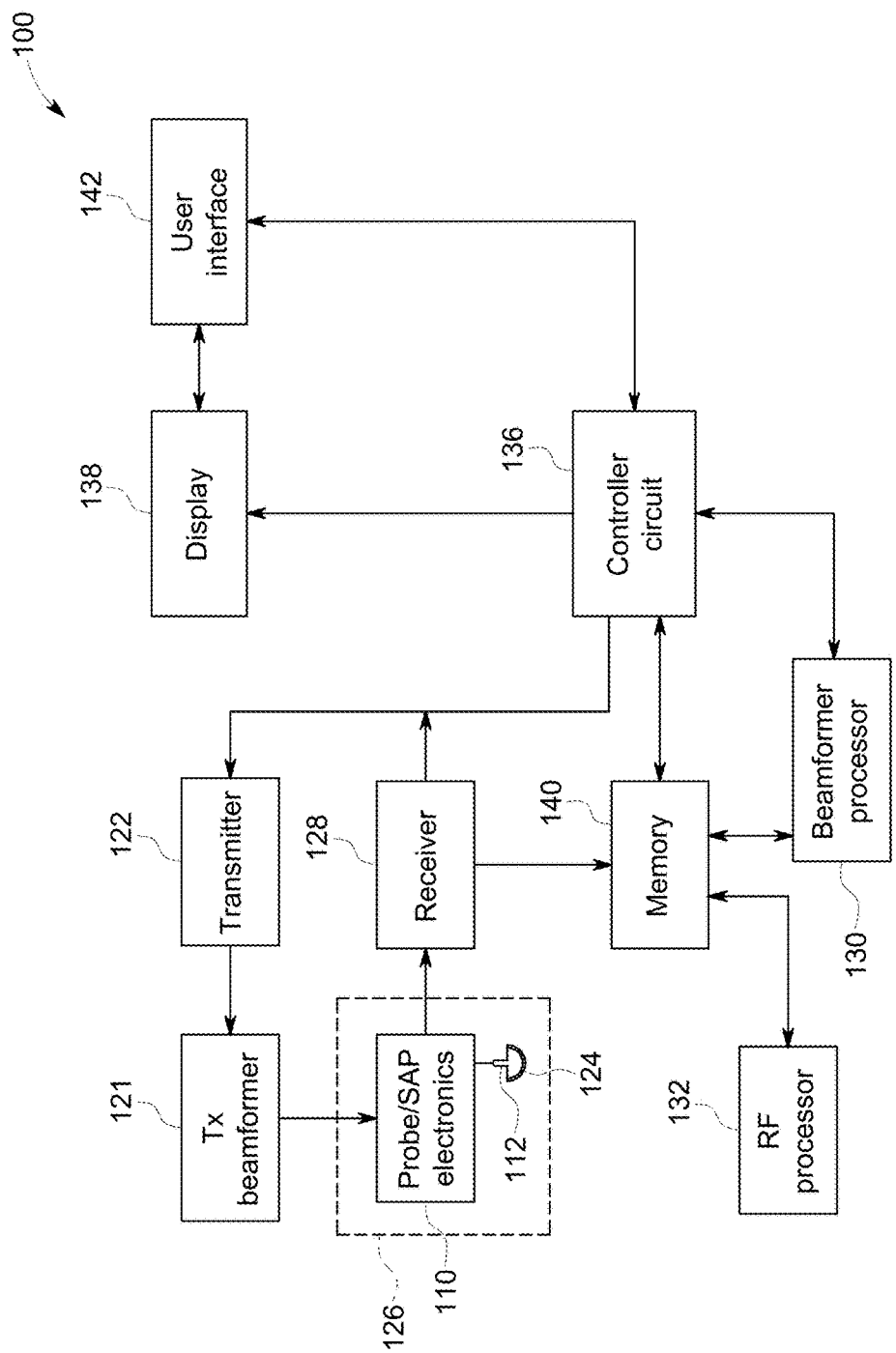
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for measuring cardiac output of a patient by acquiring multiple pulsed wave (PW) Doppler gates of a patient during a multi-gated pulsed Doppler mode. This mode configures an ultrasound probe to transmit with a wide beam profile, covering several centimeters (cm) at a standard depth of left ventricular outflow tract (LVOT), such as ten cm, and multiple parallel receive beamforming. The multi-gated pulsed Doppler mode provides PW Doppler data in the form of multiple Doppler gates (e.g., over a hundred) corresponding to spectrum data (e.g., spectrum waveform) for an area or location within a region of interest (e.g., LVOT). The PW Doppler data may be used to show velocities of moving tissue or fluids, such as blood, within an area defined by the Doppler gates. The transmissions from the ultrasound probe corresponding to the multi-gated Doppler may be interleaved with transmits for tissue imaging (e.g., B-mode), enabling live tissue imaging continues concurrently and/or in parallel with PW Doppler gate acquisition.

In various embodiments, a select gate is automatically selected from the multiple Doppler gates based on one or more characteristics of the spectrum waveform for each Doppler gate. For example, the one or more characteristics may correspond to a duration of the spectrum waveform, a velocity direction, a peak velocity, power of the spectrum waveform, change in velocity during the spectrum waveform, and/or the like. A velocity time integral (VTI) and/or a heart rate may be calculated by various embodiments from the selected Doppler gate. Optionally, a cross sectional area (CSA) of the LVOT may be estimated from a height, weight and gender of the patient, which may be used with a systolic VTI and the heart rate to calculate a cardiac output of the patient. Additionally or alternatively, the CSA may be measured automatically or manually from segmenting and/or identifying the LVOT from a tissue image (e.g., a tissue image in a parasternal long axis or PLAX view) and/or estimated by changes in spectral waveforms (e.g., velocity, power) with respect to the multiple Doppler gates within the region of interest.

A technical effect of at least one embodiment includes increased speed and accuracy in determining cardiac output of patients across multiple user technical expertise. A technical effect of at least one embodiment includes reducing the effect of user technical expertise of ultrasound measurements in calculated cardiac output of a patient.

FIG. 1 is a schematic diagram of a diagnostic medical imaging system, specifically, an ultrasound imaging system 100. The ultrasound imaging system 100 includes an ultrasound probe 126 having a transmitter 122 and probe/SAP electronics 110. The ultrasound probe 126 may be configured to acquire ultrasound data or information from a region of interest (e.g., organ, blood vessel) of the patient. The ultrasound probe 126 is communicatively coupled to the controller circuit 136 via the transmitter 122. The transmitter 122 transmits a signal to a transmit beamformer 121 based on acquisition settings received by the user. The signal transmitted by the transmitter 122 in turn drives the transducer elements 124 within the transducer array 112. The transducer elements 124 emit pulsed ultrasonic signals into a patient (e.g., a body). A variety of a geometries and configurations may be used for the array 112. Further, the array 112 of transducer elements 124 may be provided as part of, for example, different types of ultrasound probes.

The acquisition settings may define an amplitude, pulse width, frequency, and/or the like of the ultrasonic pulses emitted by the transducer elements 124. The acquisition settings may be adjusted by the user by selecting a gain setting, power, time gain compensation (TGC), resolution, and/or the like from the user interface 142.

The transducer elements 124, for example piezoelectric crystals, emit pulsed ultrasonic signals into a body (e.g., patient) or volume corresponding to the acquisition settings. The ultrasonic signals may include, for example, one or more reference pulses, one or more pushing pulses, and/or one or more pulsed wave Doppler pulses. At least a portion of the pulsed ultrasonic signals back-scatter from a region of interest (ROI) (e.g., heart, left ventricular outflow tract, breast tissues, liver tissues, cardiac tissues, prostate tissues, and the like) to produce echoes. The echoes are delayed in time and/or frequency according to a depth or movement, and are received by the transducer elements 124 within the transducer array 112. The ultrasonic signals may be used for imaging, for measuring changes in position or velocity within the ROI (e.g., movement of blood cells), differences in compression displacement of the tissue (e.g., strain), and/or for therapy, among other uses.

The transducer array 112 may have a variety of array geometries and configurations for the transducer elements 124 which may be provided as part of, for example, different types of ultrasound probes 126. The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored on memory 140, temporarily. The digitized signals correspond to the backscattered waves receives by each transducer element 124 at various times. After digitization, the signals still may preserve the amplitude, frequency, phase information of the backscatter waves.

Optionally, the controller circuit 136 may retrieve the digitized signals stored on the memory 140 to prepare for the beamformer processor 130. For example, the controller circuit 136 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 140) for beamforming calculations using any suitable beamforming method, for example, as described in U.S.

Patent Publication No. 2012/0010508, entitled, "METHOD AND SYSTEM FOR CONTROLLING COMMUNICATION OF DATA IN AN ULTRASOUND SYSTEM," which is expressly incorporated herein by reference, as well as adaptive beamforming, synthetic transmit focus, aberration correction, synthetic aperture, clutter reduction and/or adaptive noise control, and/or the like.

The beamformer processor 130 may further perform filtering and decimation, such that only the digitized signals corresponding to relevant signal bandwidth is used, prior to beamforming of the digitized data. For example, the beamformer processor 130 may form packets of the digitized data based on scanning parameters corresponding to focal zones, expanding aperture, imaging mode (B, color flow, PW Doppler), and/or the like. The scanning parameters may define channels and time slots of the digitized data that may be beamformed, with the remaining channels or time slots of digitized data that may not be communicated for processing (e.g., discarded). For example, the user may select a scanning parameter corresponding to an ROI (e.g., ROI 402 of FIG. 4) of a LVOT at a depth of approximately ten centimeters, which may reduce the number of channels beamformed by the beamformer processor 130 relative to scanning performed at deeper depths (e.g. greater than ten centimeters).

The beamformer processor 130 performs beamforming on the digitized signals and outputs a radio frequency (RF) signal. The RF signal is then provided to an RF processor 132 that processes the RF signal. The RF processor 132 may generate different ultrasound image data types, e.g. B-mode, color Doppler (velocity/power/variance), tissue Doppler (velocity), and Doppler energy, for multiple scan planes or different scanning patterns. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, on the memory 140.

Alternatively, the RF processor 132 may include a complex demodulator (not shown) that demodulates the RF signal to form IQ data pairs representative of the echo signals. The RF or IQ signal data may then be provided directly to the memory 140 for storage (e.g., temporary storage). Optionally, the output of the beamformer processor 130 may be passed directly to the controller circuit 136.

The controller circuit 136 may be configured to process the acquired ultrasound data (e.g., RF signal data or IQ data pairs) and prepare frames of ultrasound image data for display on the display 138. The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140).

The controller circuit 136 is configured to perform one or more processing operations according to a plurality of selectable ultrasound modalities on the acquired ultrasound data, adjust or define the ultrasonic pulses emitted from the transducer elements 124, adjust one or more image display settings of components (e.g., ultrasound images, interface components, positioning regions of interest) displayed on the display 138, and other operations as described herein. Acquired ultrasound data may be processed in real-time by the controller circuit 136 during a scanning or therapy session as the echo signals are received. Additionally or alternatively, the ultrasound data may be stored temporarily on the memory 140 during a scanning session and processed in less than real-time in a live or off-line operation.

The memory 140 may be used for storing processed frames of acquired ultrasound data that are not scheduled to be displayed immediately or to store post-processed images, firmware or software corresponding to, for example, a graphical user interface, one or more default image display settings, programmed instructions (e.g., for the controller circuit 136, the beamformer processor 130, the RF processor 132), and/or the like. The memory 140 may be a tangible and non-transitory computer readable medium such as flash memory, RAM, ROM, EEPROM, and/or the like.

The memory 140 may store 3D ultrasound image data sets of the ultrasound data, where such 3D ultrasound image data sets are accessed to present 2D and 3D images. For example, a 3D ultrasound image data set may be mapped into the corresponding memory 140, as well as one or more reference planes. The processing of the ultrasound data, including the ultrasound image data sets, may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored on the memory 140 or currently being acquired, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142.

For example, a portion of the user interface 142 may correspond to a graphical user interface (GUI) generated by the controller circuit 136 shown on the display. The GUI may include one or more interface components that may be selected, manipulated, and/or activated by the user operating the user interface 142 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 100 performed by the controller circuit 136.

Figure 2:
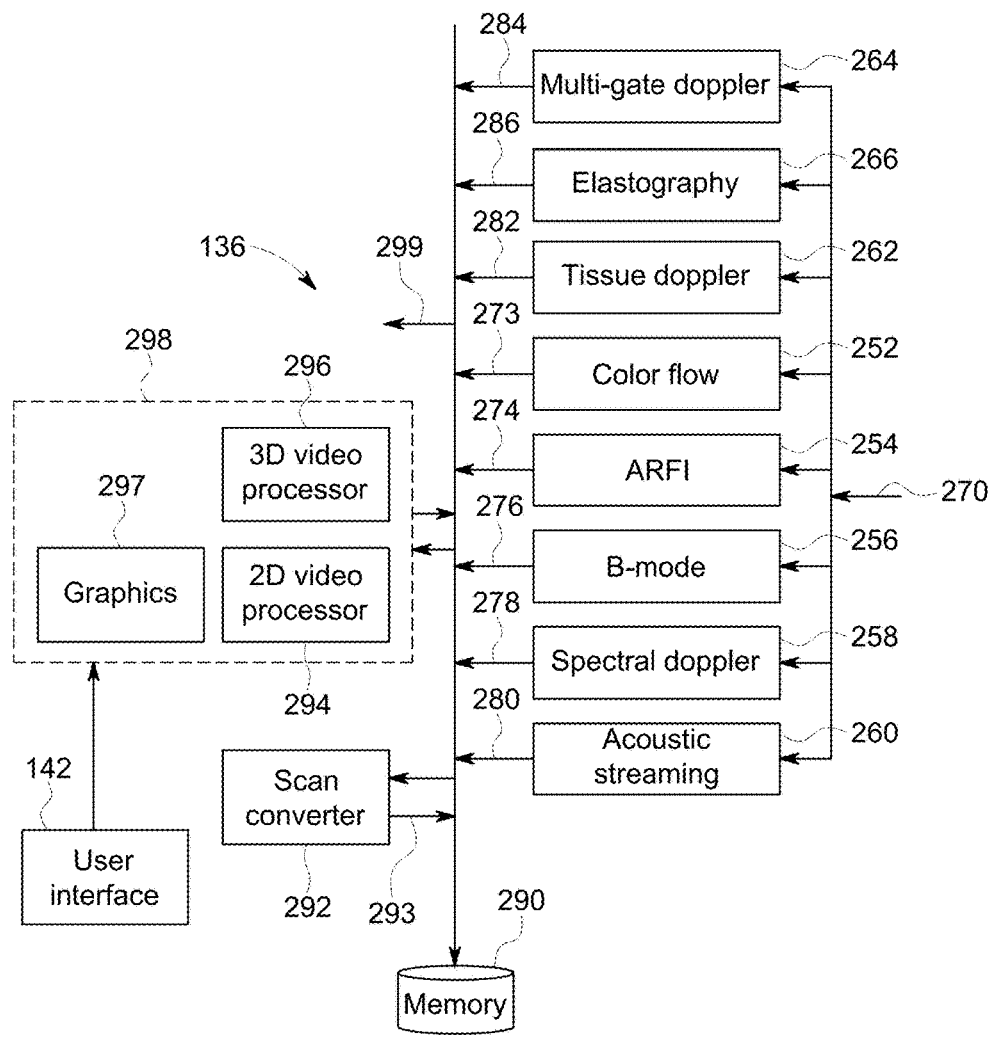
FIG. 2 is an illustration of a simplified block diagram of a controller circuit of the ultrasound imaging system of FIG. 1, in accordance with an embodiment.

FIG. 2 is an exemplary block diagram of the controller circuit 136. The controller circuit 136 is illustrated in FIG. 2 conceptually as a collection of circuits and/or software modules, but may be implemented utilizing any combination of dedicated hardware boards, DSPs, one or more processors, FPGAs, ASICs, a tangible and non-transitory computer readable medium configured to direct one or more processors, and/or the like.

The circuits 252-266 perform mid-processor operations representing one or more software features of the ultrasound imaging system 100. The controller circuit 136 may receive ultrasound data 270 in one of several forms. In the embodiment of FIG. 1, the received ultrasound data 270 constitutes IQ data pairs representing the real and imaginary components associated with each data sample of the digitized signals. The IQ data pairs are provided to one or more circuits, for example, a color-flow circuit 252, an acoustic radiation force imaging (ARFI) circuit 254, a B-mode circuit 256, a spectral Doppler circuit 258, an acoustic streaming circuit 260, a tissue Doppler circuit 262, a multi-gate Doppler circuit 264, and an electrography circuit 266. Other circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

Each of circuits 252-266 is configured to process the IQ data pairs in a corresponding manner to generate, respectively, color-flow data 273, ARFI data 274, B-mode data 276, spectral Doppler data 278, acoustic streaming data 280, tissue Doppler data 282, multiple PW Doppler gate data 284 (e.g., ROI data acquisition location), electrography data 286 (e.g., strain data, shear-wave data), among others, all of which may be stored in a memory 290 (or the memory 140 shown in FIG. 1) temporarily before subsequent processing. The data 273-286 may be stored, for example, as sets of vector data values, where each set defines an individual ultrasound image frame. The vector data values are generally organized based on the polar coordinate system.

A scan converter circuit 292 accesses and obtains from the memory 290 the vector data values associated with an image frame and converts the set of vector data values to Cartesian coordinates to generate an ultrasound image frame 293 formatted for display. The ultrasound image frames 293 generated by the scan converter circuit 292 may be provided back to the memory 290 for subsequent processing or may be provided to the memory 140. Once the scan converter circuit 292 generates the ultrasound image frames 293 associated with the data, the image frames may be stored in the memory 290 or communicated over a bus 299 to a database (not shown), the memory 140, and/or to other processors (not shown).

The display circuit 298 accesses and obtains one or more of the image frames from the memory 290 and/or the memory 140 over the bus 299 to display the images onto the display 138. The display circuit 298 receives user input from the user interface 142 selecting one or image frames to be displayed that are stored on memory (e.g., the memory 290) and/or selecting a display layout or configuration for the image frames.

The display circuit 298 may include a 2D video processor circuit 294. The 2D video processor circuit 294 may be used to combine one or more of the frames generated from the different types of ultrasound information. Successive frames of images may be stored as a cine loop (4D images) in the memory 290 or memory 140. The cine loop represents a first in, first out circular image buffer to capture image data that is displayed in real-time to the user. The user may freeze the cine loop by entering a freeze command at the user interface 142.

The display circuit 298 may include a 3D processor circuit 296. The 3D processor circuit 296 may access the memory 290 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

The display circuit 298 may include a graphic circuit 297. The graphic circuit 297 may access the memory 290 to obtain groups of ultrasound image frames and the ROI data acquisition locations that have been stored or that are currently being acquired. The graphic circuit 297 may generate images that include the images of the ROI and a graphical representation positioned (e.g., overlaid) onto the images of the ROI. The graphical representation may represent an outline of a treatment space, the focal point or region of the therapy beam, a path taken by the focal region within the treatment space, a probe used during the session, the ROI data acquisition location, and the like. Graphical representations may also be used to indicate the progress of the therapy session. The graphical representations may be generated using a saved graphical image or drawing (e.g., computer graphic generated drawing), or the graphical representation may be directly drawn by the user onto the image using a GUI of the user interface 142.

In connection with FIG. 3, the user may select an interface component corresponding to a cardiac output measurement via the user interface 142. When the interface component is selected, the controller circuit 136 may enter a multi-gated Doppler gate mode to measure a cardiac output of the patient.

Figure 3A:
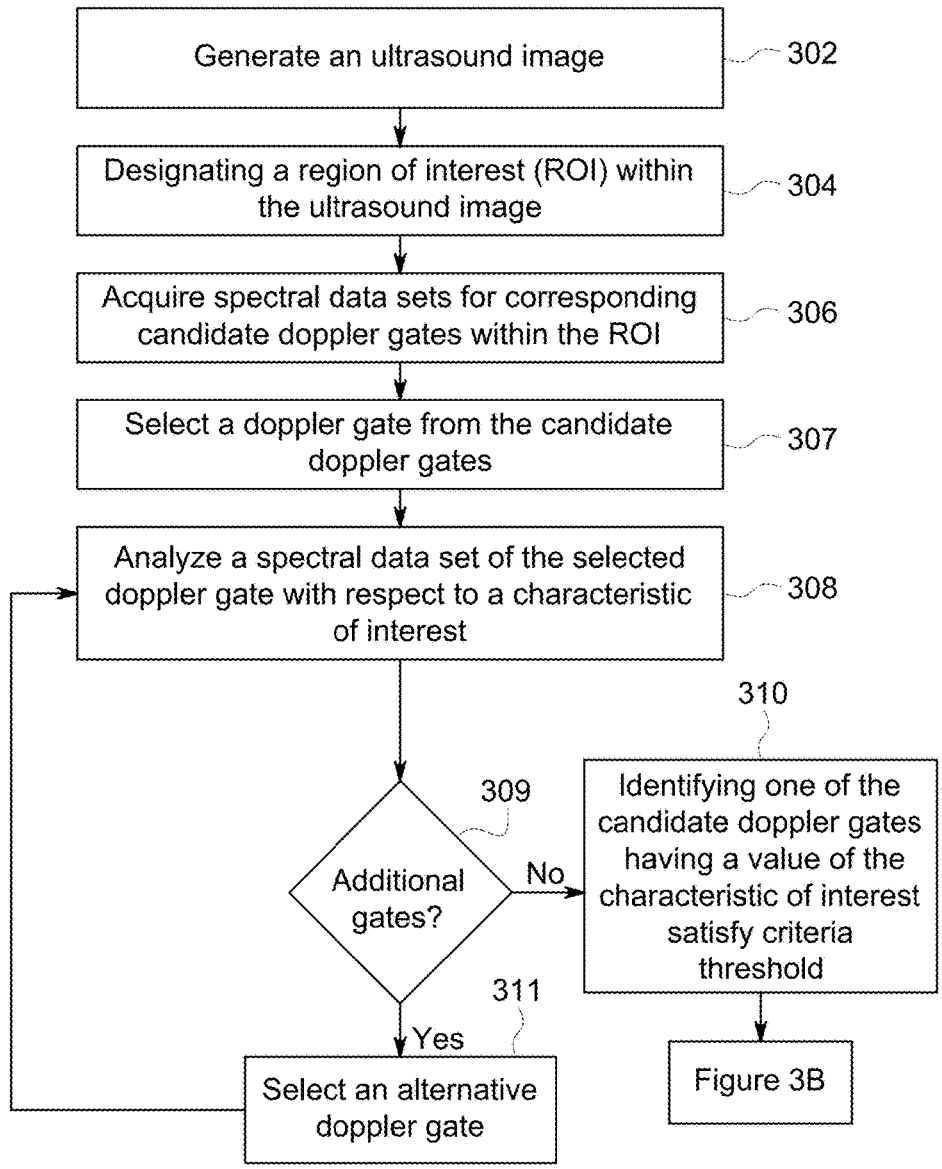
FIGS. 3A-B illustrate a flowchart of a method for measuring a cardiac output, in accordance with an embodiment.
Figure 3B:
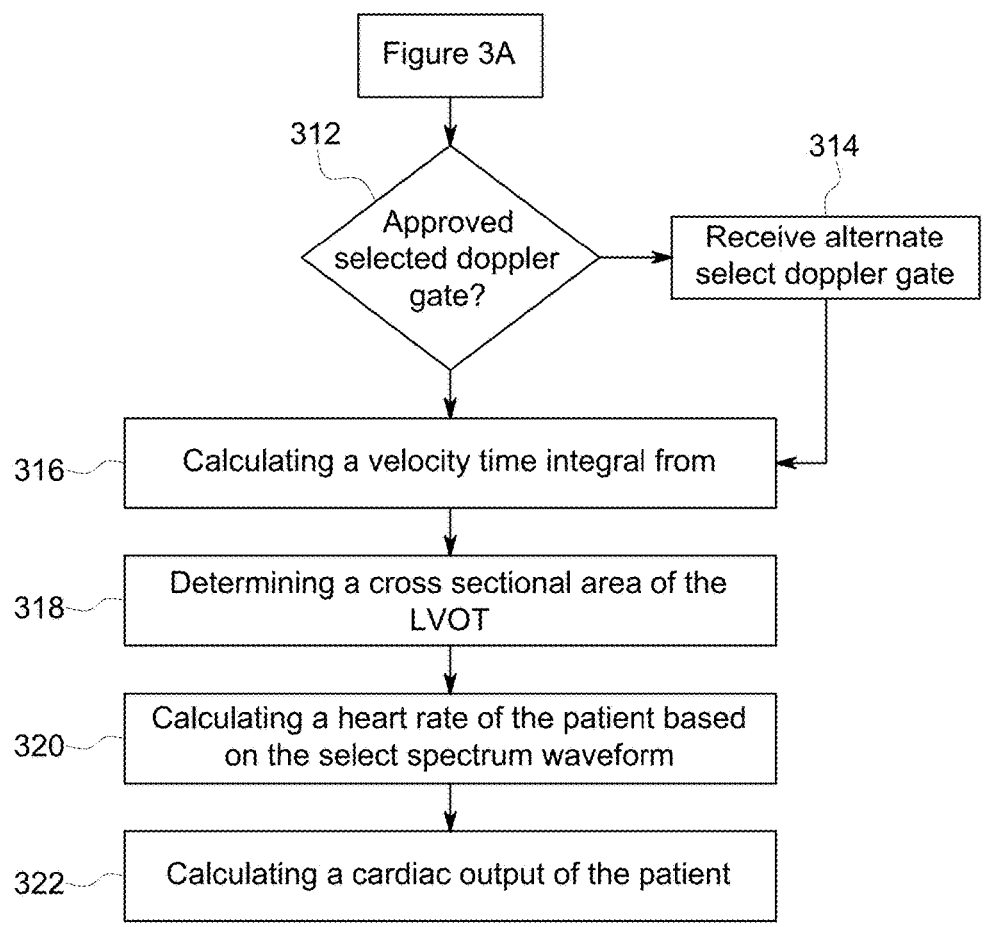

FIGS. 3A-B illustrate a flowchart of a method 300 for measuring a cardiac output, in accordance with various embodiments described herein. The method 300, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms stored on a tangible non-transitory computer readable medium (e.g., one or more computer software modules) to direct hardware (e.g., one or more processors) to perform one or more operations described herein. It should be noted, other methods may be used, in accordance with embodiments herein.

One or more methods may (i) generate an ultrasound image based on ultrasound imaging data of a patient acquired by an ultrasound probe, (ii) automatically designate a region of interest (ROI) within the ultrasound image, (iii) acquire spectral data sets for corresponding candidate Doppler gates within the ROI based on Doppler data acquired by the ultrasound probe, (iv) automatically identify a select Doppler gate from the candidate Doppler gates based on a characteristic of the spectral data sets, and (v) calculate a cardiac output of the patient based on the select spectrum waveform.

Beginning at 302, the controller circuit 136 generates an ultrasound image 400. In connection with FIG. 4, the ultrasound image 400 may be generated based on ultrasound imaging data of a patient acquired by the ultrasound probe 126.

Figure 4:
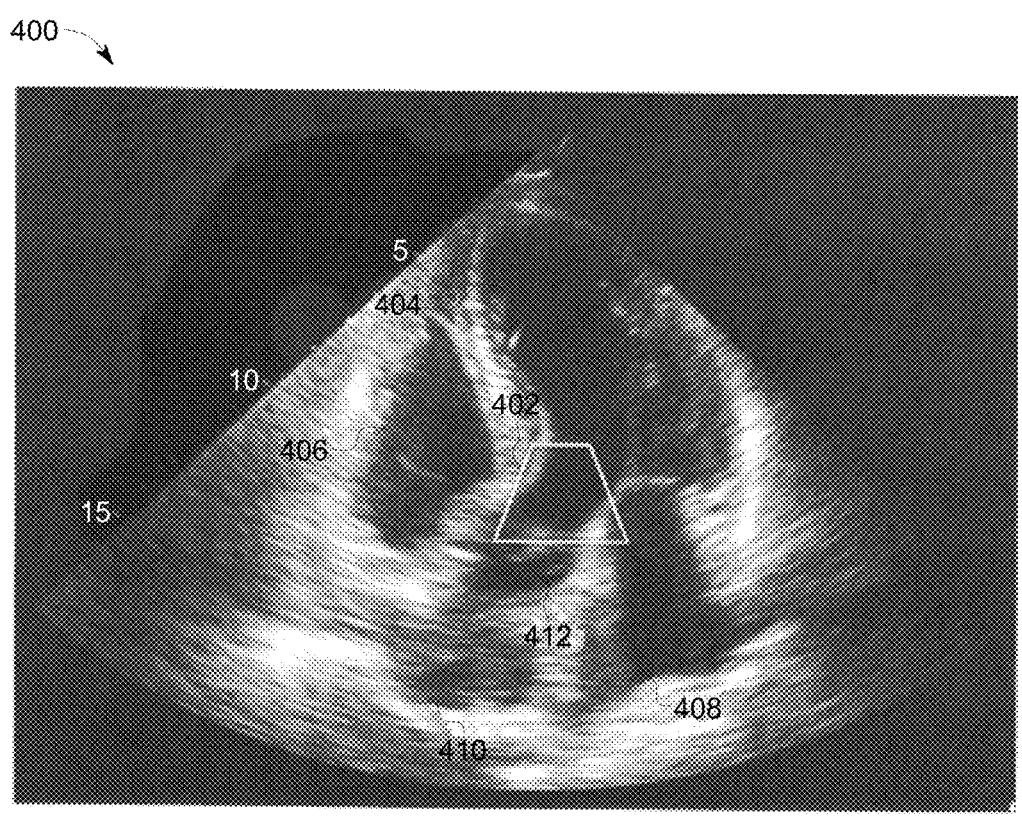
FIG. 4 is an illustration of an ultrasound image, in accordance with an embodiment.

FIG. 4 illustrates the ultrasound image 400 of a five chamber view of a heart of the patient. For example, the user may position the ultrasound probe 126 to align the transducer array 112 along an apical long axis of the heart. The ultrasound acquisition settings of the ultrasound probe 126 may be selected from the user using the user interface 142 (FIG. 1). For example, the user may define the gain, power, time gain compensation (TGC), resolution, and/or the like of the ultrasound probe 126 using the user interface 142 by selecting one or more interface components of the GUI shown on the display 138. Additionally or alternatively, the ultrasound acquisition settings may be based on a selection of an interface component corresponding to one or more of the circuits 250-266. For example, the user may select a B-mode acquisition interface component, which instructs the controller circuit 136 to configure the ultrasound acquisition settings of the ultrasound probe 126 and process received ultrasound imaging data to produce B-mode data 276 by the B-mode circuit 256. Based on the ultrasound acquisition settings, the transducer elements 124 of the ultrasound probe 126 emit the ultrasonic pulses along the apical long axis of the heart of the patient, of which, at least a portion of the pulsed ultrasonic signals back-scatter from portions of the heart to produce echoes and are received by the transducer elements 124. The transducer elements 124 convert the received echo signals into electrical signals which may be received by the controller circuit 136 as described in reference to FIG. 1.

Returning to FIG. 3A, at 304 the controller circuit 136 may designate a region of interest (ROI) 402 within the ultrasound image 400. The ROI 402 may correspond to an area to acquire velocity information (e.g., Doppler data) within the ultrasound image 400, such as the LVOT, to measure blood pumped from a ventricle of the heart. In connection with FIG. 4, the controller circuit 136 may automatically overlay a ROI 402 on the ultrasound image 400 based on a selection of one or more interface components.

For example, the GUI may include an interface component corresponding to a cardiac output measurement. When selected by the user, the controller circuit 126 may automatically place the ROI 402 by executing a classification algorithm. The classification algorithm may be stored in the memory 140, and correspond to a machine learning algorithm based on a classifier algorithm (e.g., random forest classifier) or segmentation algorithm (e.g., real time tracking contour tracking library) based on priori information. The classification algorithm utilizes a pixel level classifier to determine a region within the ultrasound image 400 corresponding to an outflow tract, such as the LVOT. The classification algorithm may determine chambers of the ultrasound image 400 from a feature space of the pixels based on various intensities and/or spatial position of pixels of the ultrasound image 400.

The controller circuit 136 by executing the classification algorithm (may determine) forming individual chambers 404-410 based on changes in pixel intensities. For example, the chambers 404-410 are represented as a cluster of low intensity pixels. Surrounded by relatively high intensity pixels (e.g., representing the septum). For example, since the chamber 404 is larger relative to the remaining chambers 406-410, the controller circuit 136 may determine that the chamber 404 corresponds to the left ventricle. Based on the spatial position of the adjacent chambers 406-408 and 412 to the chamber 404 and within the ultrasound image 400, the controller circuit 136 may classify the chamber 406-408 and 412. For example, since the chamber 406 is positioned adjacent and approximately parallel along a horizontal axis to the chamber 404, the controller circuit 136 may classify the chamber 406 as the right ventricle. In another example, since the chamber 412 is centrally positioned within the ultrasound image 400 and/or is adjacent to all of the chambers 404-410, the controller circuit 136 may classify the chamber 412 as the aortic valve.

Based on the classification of the chamber 404 and the chamber 412 as the left ventricle and aortic valve, respectively, the controller circuit 136 may designate or define the ROI 402 on the ultrasound image 400 corresponding to an outflow tract, such as the LVOT. For example, the controller circuit 136 may determine that a portion of the left ventricle adjacent to the chamber 412, identified as the aortic valve, corresponds to an outflow tract of the left ventricle, and designate the ROI 402 at the portion of the chamber 412. Optionally, a size of the ROI 402 may be adjusted by the controller circuit 136 to conform to boundaries (e.g. septum represented at the higher intensity pixels) of the chamber 404.

Optionally, the controller circuit 136 may adjust a position of the ROI 402 based on a user selection received via the user interface 142. For example, the user may select to reposition the ROI 402 with respect to the ultrasound image 400. In another example, the user may select a portion of the ROI 402 (e.g., one of the sides) to adjust an overall size of the ROI 402 with respect to the ultrasound image 400.

Additionally or alternatively, the user may designate a position of the ROI 402. For example, the user may outline an area of the ultrasound image 400 via the user interface 142 to define or designate a position of the ROI 402.

Returning to FIG. 3A, at 306 the controller circuit 136 may acquire spectral data sets for corresponding candidate Doppler gates within the ROI 402. In connection with FIG. 1, the controller circuit 136 may direct the ultrasound probe 126 to transmit parallel ultrasonic pulses from the transducer elements 124 within the ROI 402. For example, the controller circuit 136 may direct the transducer elements 124 to scan across the ROI 402 (in both X and Y directions), emitting and receiving echo signals, corresponding to Doppler data, of one or more locations, specifically Doppler gates, within the ROI 402.

Figure 5:
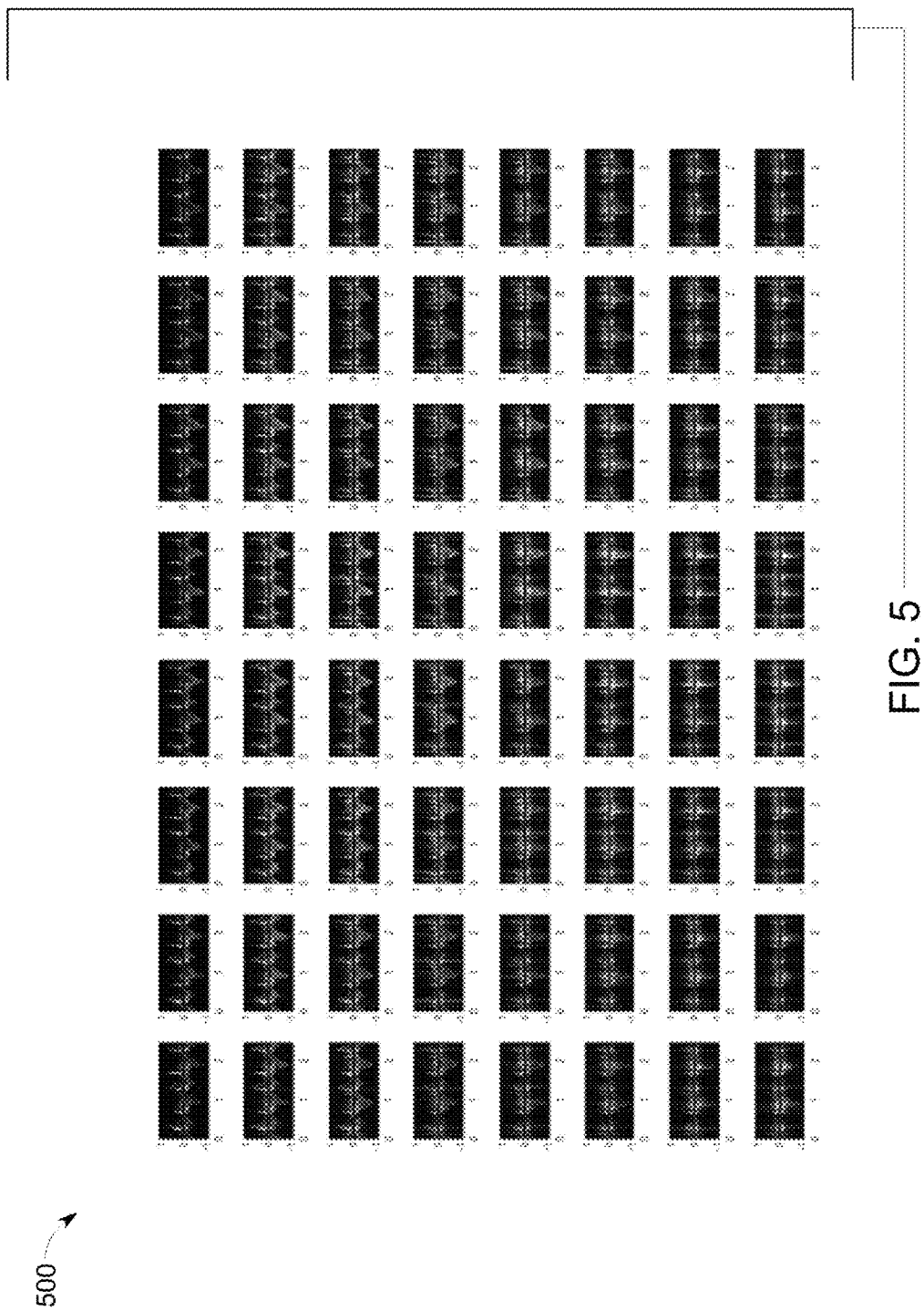
FIG. 5 is an illustration of a portion of Doppler gates acquired within a region of interest, in accordance with an embodiment.

In various embodiments, in connection with FIG. 5, the controller circuit 136 may instruct the transducer elements 124 to emit a wide transmit beam utilizing a parallel or multiline acquisition (MLA) technique to acquire multiple Doppler gates within the ROI 404.

FIG. 5 illustrates a portion of the Doppler gates 500 acquired within the ROI 402. The controller circuit 136 may instruct the transducer elements 124 to emit a wide transmit beam having 128 pulse trains (e.g., packet size) covering an area of two centimeters based on a size of the ROI 402. The receiver 128 may receive echo signals from sixteen parallel beams, which are converted into digitized data. The beamform processor 130 isolates the digitized data (e.g., time slots) based on a depth of the ROI 402 (e.g., ten centimeters), and beamforms the selected digitized data, which corresponds to one or more spectral data sets. For example, the digitized data may include twenty five Doppler gates per beam or 400 Doppler gates measured from the wide transmit beam stored as Doppler data in the memory 140.

Each of the Doppler gates 500 include a spectral data set corresponding to a spectrum of velocities over time. The spectrum data set may correspond to change in movement (e.g., blood flow) measured within the corresponding Doppler gates 500 over time. It should be noted that in various embodiments the area covered by the transmit beam may be wider than two centimeters or slimmer than two centimeters. Additionally, it should be noted that in various embodiments the depth may be greater than ten centimeters or less than ten centimeters.

Additionally or alternatively, the ultrasound imaging data and the Doppler data are interleaved when acquired by the ultrasound probe 126. For example, in connection with FIG. 6, acquisition time periods 602a-602n of the ultrasound probe 126 may be subdivided into alternating frames corresponding to acquisition of Doppler data 612, 614 or ultrasound imaging data 606-610.

Figure 6:
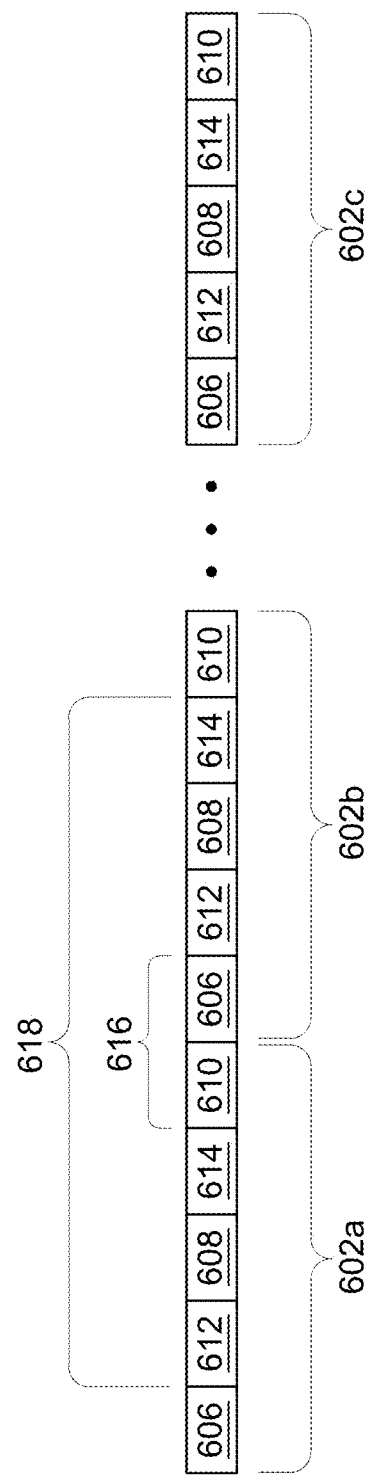
FIG. 6 is an illustration of a diagram of acquisition time periods formed by interleaved frames corresponding to Doppler data or ultrasound imaging data.

FIG. 6 illustrates the acquisition time periods 602a-602n each representing an amount of time (e.g., thirty milliseconds, fifteen millisecond) for the ultrasound probe 126 to acquire an amount of ultrasound imaging data and Doppler data for the controller circuit 136 to generate a frame of an ultrasound image, such as the ultrasound image 400, and the Doppler gates 508 within the ROI 402. During each of the acquisition time periods 602a-602n the controller circuit 136 may instruct the transducer array 124 to switch between transmitting and receiving ultrasound signals during frames e.g., 606-614 of the acquisition time periods 602a-602n. For example, frames 612-614 corresponding to acquisition of Doppler data are interposed and/or positioned between frames 606-610 corresponding to acquisition of ultrasound imaging data. Each frame may correspond to a predetermined amount of time within the acquisition time period 602a-602n the ultrasound probe 126 acquires ultrasound imaging data (e.g., frames 606-610) or Doppler data (e.g., frames 612-614).

For example, at the start of the acquisition time period 602a, during the frame 606, the controller circuit 136 may instruct the transducer elements 124 of the ultrasound probe 126 to emit ultrasound signals (e.g., such pulses or waves) to acquire ultrasound imaging data, which will be processed by the B-mode circuit 256. Optionally, the controller circuit 136 may stop transmission of the ultrasound signals within the frame 606 to ensure that received echoes reflected by tissue in response to the ultrasound signals for the ultrasound imaging data are not received by the ultrasound probe 126 during the subsequent frame, the frame 612. During the frame 612, the controller circuit 126 may instruct the transducer elements 124 to emit ultrasound signals (e.g., firings) to acquire Doppler data from the ROI 402, for example a wide transmit beam having 128 pulse trains (e.g., packet size), which will be process by the multi-gate Doppler circuit 264.

It should be noted that although acquisition of the ultrasound imaging data and the Doppler data occurs at corresponding frames 606-614, the B-mode circuit 256 and the multi-gate Doppler circuit 264, or generally the controller circuit 136, may process the data independently over multiple frames. For example, the controller circuit 136 may process the Doppler data independently while ultrasound imaging data is being acquired by the ultrasound probe 126 during subsequent frames.

Optionally, the controller circuit 136 may define the acquisition time periods 602a-602n, such as a duration of the frames 606-610, to allow acquisition of Doppler data at equal intervals to maintain a time scale (e.g., frequency) of the Doppler data acquisition. For example, a duration of the frames 606 and 610, defining a beginning and end of the acquisition time periods 602a-602n, are half of a duration of the frame 608. Specifically, the duration 616 of the combined frames 606 and 610 are approximately the same as the duration of the frame 608. Thereby, over multiple acquisition time periods 602a-602b, such as a period of time 618, the frames 612-614 corresponding to acquisition of Doppler data occur periodically at set intervals defined by the duration of the frame 608 and the duration 616 (e.g., combination of the frames 606 and 610).

Returning to FIG. 3A, at 307 the controller circuit 136 may select a Doppler gate from the candidate Doppler gates. For example, the controller circuit 136 may select the Doppler gate 502 to perform additional analysis.

At 308 the controller circuit 136 may analyze a spectral data set of the selected Doppler gate 502 with respect to a characteristic of interest. In connection with FIG. 7, the spectral data set may be plotted to form a spectral waveform. The characteristic of interest may be based on a morphology of the spectrum waveform, such as a duration (e.g., length of the spectrum waveform), a direction, a peak velocity, power, and/or change in velocity. The morphology may correspond to a peak amplitude, a number of peaks, peak width, peak latency, intensity of the pixels within the spectrum waveform, descending and/or ascending slopes, and/or the like. The morphology of the spectrum waveform may be determined by the controller circuit 136, for example, based on changes in the spectrum waveform overtime.

Figure 7:
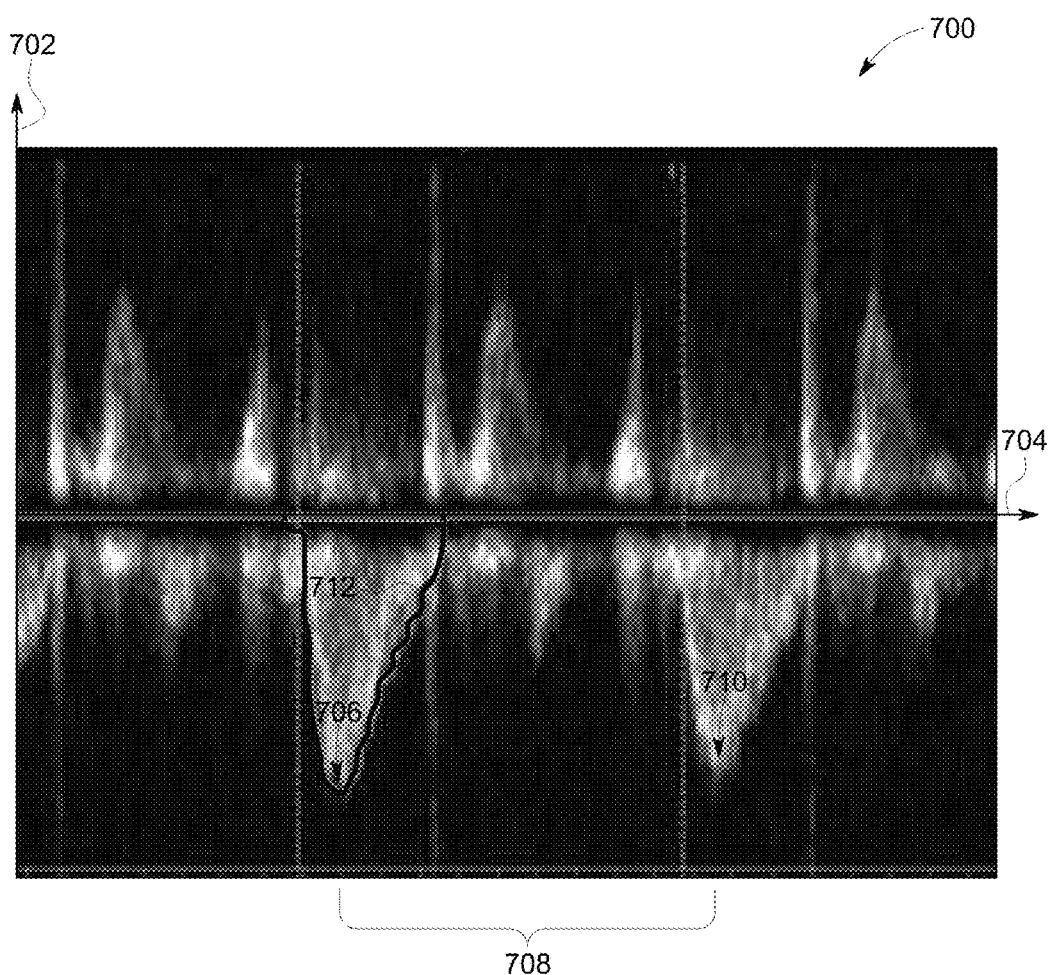
FIG. 7 is an illustration of a spectrum waveform of a select Doppler gate, in accordance with an embodiment.

FIG. 7 illustrates a spectrum waveform 700 of the selected Doppler gate 502. The spectrum waveform 700 is plotted along a vertical axis 702 representing frequency (e.g., corresponding to a velocity) over time represented by a horizontal axis 704. The controller circuit 136 may determine a direction of the blood flow based on magnitudes of the spectrum waveform 700. For example, portions of the spectrum waveform 700 having a positive magnitude (e.g., above the horizontal axis 704) represents movement of blood flow, corresponding to a velocity, moving and/or directed towards the ultrasound probe 126, and portions of the spectrum waveform 700 having a negative magnitude (e.g., below the horizontal axis 704) represents movement of blood flow, corresponding to a velocity, moving and/or directed away from the ultrasound probe 126.

The controller circuit 136 may determine a peak velocity based on a magnitude or vertex of one or more peaks of the spectrum waveform 700. The peak velocity may correspond to a phase of the cardiac cycle represented by the spectrum waveform 700. For example, the controller circuit 136 may determine a peak systolic velocity or when the systole phase of the cardiac cycle occurs by identifying the vertex of the negative peak 706. The controller circuit 136 may determine when a peak occurs based on changes in slope magnitudes corresponding to a vertex. For example, a change from a negative slope to a positive slope of the spectrum waveform 700 may indicate a negative peak. Additionally or alternatively, the controller circuit 136 may take a derivative of the spectrum waveform 700 to determine vertexes of peaks, which have a value of zero.

The controller circuit 136 may determine a power of the spectrum waveform 700 based on an intensity of the pixels forming the spectrum waveform 700. The power of the spectrum waveform 700 may correspond to an overall strength of the Doppler data represented by the spectrum waveform 700. For example, the controller circuit 136 may determine an average pixel intensity of the spectrum waveform 700, which corresponds to a power of the spectrum waveform 700. Additionally or alternatively, the controller circuit 136 may compare the average pixel intensity with a power scale stored on the memory 140 to determine a power value of the spectrum waveform 700.

The controller circuit 136 may determine a change in velocity by comparing changes in magnitude or vertexes of subsequent peaks. The change in velocity may correspond to changes in velocity of the blood flow between two adjacent cardiac cycles. For example, the negative peaks 706 and 710 each may correspond to a systole velocity during the systole of different cardiac cycles. The controller circuit 136 may compare the magnitudes of vertexes of the negative peaks 706 and 710 to determine changes in velocity of the spectrum waveform 700.

Additionally or alternatively, the controller circuit 136 may calculate a mean velocity of the spectral data set. For example, the controller circuit 136 may calculate an average amplitude for the spectrum waveform 700 over time, which corresponds to the mean velocity of the spectral data set.

Returning to FIG. 3A, at 309 the controller circuit 136 may determine whether additional candidate Doppler gates need to be analyzed at 308. For example, when the controller circuit 136 determines that one or more spectrum data sets of a Doppler gate has not been analyzed with respect to the characteristic of interest, the controller circuit 136 may select one of the remaining or alternative Doppler gates at 311 and return to 308.

When the controller circuit 136 determines at 309 that no additional Doppler gates need to be analyzed, at 310, the controller circuit 136 may identify one of the candidate Doppler gates having a value of the characteristic of interest that satisfies a criteria threshold. The value of the characteristic of interest may correspond to the value of the characters of interest determined at 308. For example, when the characteristic of interest is the peak velocity, the value may be the peak velocity of the candidate Doppler gate. The criteria threshold may be based on one of the candidate Doppler gates.

For example, the controller circuit 136 may define an initial criteria threshold as the value of the characteristic of interest for a first candidate Doppler gate. The controller circuit 136 may compare a value of the characteristic of interest from an alternative candidate Doppler gate to determine which of the candidate Doppler gates to select for subsequent measurements (e.g., at 322 cardiac output measurement). If the value of the alternative candidate Doppler gate exceeds the criteria threshold, the controller circuit 136 may adjust the criteria threshold to match the value of the alternative candidate Doppler gate and continually compare the values of the Doppler gates to identify the candidate Doppler gate, which may correspond to the candidate Doppler gate used for the criteria threshold. For example, the controller circuit 136 may identify a candidate Doppler gate having a spectrum waveform with a power, duration, and/or a peak velocity greater than the remaining spectrum waveforms of the other candidate Doppler gates.

Additionally or alternatively, the criteria threshold may be a predetermined threshold stored in the memory 140. For example, the controller circuit 136 may select the Doppler gate based on which candidate Doppler gate has one or more characteristics of interest above the criteria threshold. For example, the characteristic interest may correspond to power, duration, peak velocity, and changes in velocity between peaks. The controller circuit 136 may select a Doppler gate having more values above the criteria threshold relative to the candidate Doppler gates.

Optionally, the controller circuit 136 may adjust a size of the ROI 402 based on the candidate Doppler gates. For example, the controller circuit 136 may omit portions of the ROI 402 corresponding to candidate Doppler gates having values that are not within a set threshold of the criteria threshold. For example, if the spectrum waveform is below a predetermined power and/or velocity threshold the controller circuit 136 may adjust and/or reduce a size of the ROI 402 to not include the location of the corresponding candidate Doppler gate.

Additionally or alternatively, the controller circuit 136 may display indicia (e.g., numerical values, graphics) indicative of one or more characteristics (e.g., the systolic velocity, mean velocity, spectral power) of the candidate Doppler gates within the ROI 402 based on the analysis of the spectral data sets. In various embodiments, the one or more characteristics may be from the spectral data sets of the candidate Doppler gates, such as the characteristic of interest. For example, the controller circuit 136 may determine a color representing a systolic velocity, a mean velocity, and/or spectral power of each candidate Doppler gate based on one or more characteristics of the spectral data sets. The controller circuit 136 may include the color information to corresponding pixels within the ROI 402 that represent a position of a candidate Doppler gate. For example, the controller circuit 136 may overlay colors corresponding to one or more characteristics of the spectral data sets candidate Doppler gates on the ultrasound image 400. In another example, the controller circuit 136 may color blend the ultrasound image 400 corresponding to one or more characteristics of the candidate Doppler gates.

In connection with FIG. 3B, at 312, the controller circuit 136 determines whether the selected Doppler gate is approved by the user. For example, the controller circuit 136 may select the spectrum waveform 700 (FIG. 7) at 310, and display the spectrum waveform 700 on the display concurrently with a corresponding position of the selected Doppler gate within the ROI 402. The controller circuit 136 may display a notification on the display 138, for example a pop-up window of the GUI having one or more interface components. The user may select one of the interface components to confirm and/or adjust the selected Doppler gate via the user interface 142.

Optionally, at 314 the controller circuit 136 may receive an alternative and/or another select Doppler gate from the remaining candidate Doppler gates. In various embodiments, the controller circuit 136 may receive a replacement or alternative select Doppler gate via the user interface 142. For example, the user may select another Doppler gate by selecting a location corresponding to an alternative candidate Doppler gate within the ROI 402. In another example, the controller circuit 136 may display the portion of the candidate Doppler gates 500 approximate and/or adjacent to the select Doppler gate, allowing the user to select one of the displayed candidate Doppler gates as the alternative and/or new select Doppler gate.

At 316, the controller circuit 136 may calculate a velocity time integral (VTI) based on the select spectrum waveform (e.g., the spectrum waveform 700). The VTI may be calculated by the controller circuit 136 from one of the peaks 706 and 710 of the spectrum waveform 700. In connection with FIG. 7, the controller circuit 136 may trace one of the peaks 706, 710 to form an envelope 712 and/or boundary of the peak by executing a contour algorithm (e.g., active contour model, snake) stored in the memory 140. For example, when executing the contour algorithm, the controller circuit 136 may identify an edges and/or boundary of the peak 706 based on changes in pixel intensities and by the horizontal axis 704 forming the envelope 712.

Additionally or alternatively, the contour circuit 136 may trace one of the peaks 706, 710 based on signals received by the user interface 142. For example, the user may trace the peak 706 to form the envelope 712 using the user interface 142, which is received by the controller circuit 136.

When the envelope 712 is formed, the controller circuit 136 may calculate a VTI from the envelope 712. For example, the controller circuit 136 may integrate and/or calculate an area of the envelope 712 to determine the VTI, and store the VTI in the memory 140. Optionally, the controller circuit 136 may display the VTI on the display 138 for the user, for example, adjacent to and/or within the ROI 402.

Returning to FIG. 3B, at 318, the controller circuit 136 may determine a cross sectional area (CSA) of the LVOT. For example, the CSA may be calculated by the controller circuit 136 by measuring an area of the LVOT within the ROI 402. In various other embodiments, the CSA of the LVOT may be determined based on demographical features of the patient.

For example, the ROI 402 may include and/or correspond to the LVOT of the patient. The controller circuit 136 may receive one or more demographical characteristics of the patient that may include at least one of a height, weight, or gender of the patient. For example, the controller circuit 136 may receive the one or more demographical characteristics from the user interface 142, received remotely from a Digital Imaging and Communications in Medicine worklist, and/or the like. The controller circuit 136 may compare the one or more demographical characteristics with an anatomical database stored on the memory 140. The anatomical database may be a collection of candidate CSAs of the LVOT with corresponding demographical characteristics. The controller circuit 1367 may select one of the candidate CSAs that match the demographical characteristics of the patient for the ROI 402.

At 320, the controller circuit 136 may calculate a heart rate of the patient based on the select spectrum waveform (e.g., the spectrum waveform 700). In connection with FIG. 7, the controller circuit 136 may calculate a heart rate based on peaks (e.g., the peaks 706 and 710) of the spectrum waveform 700. For example, the peaks 706 and 710 occur during different cardiac cycles, specifically during the systole phase of a cardiac cycle. The controller circuit 136 may determine a difference in time between the peaks 706 and 710, which corresponds to a length and/or period 708 of the cardiac cycle of heart. Based on the length 708 of the cardiac cycle, the controller circuit 136 may determine a heart rate of the patient. For example, to calculate the heart rate in beats per minutes, the controller circuit 136 may divide sixty by the length 708 in seconds of the cardiac cycle.

At 322, the controller circuit 136 may calculate a cardiac output of the patient. The cardiac output may be calculated by the controller circuit 136 based on Equation 1 shown below. The cardiac output, represented by the variable Q, may be calculated by the controller circuit 136 from the product of the VTI determined at 316, the CSA determined at 318, and the heart rate, represented by the variable HR, determined at 320.

$$Q = VTI \times CSA \times HR \quad \text{Equation (1)}$$

Figure 8:
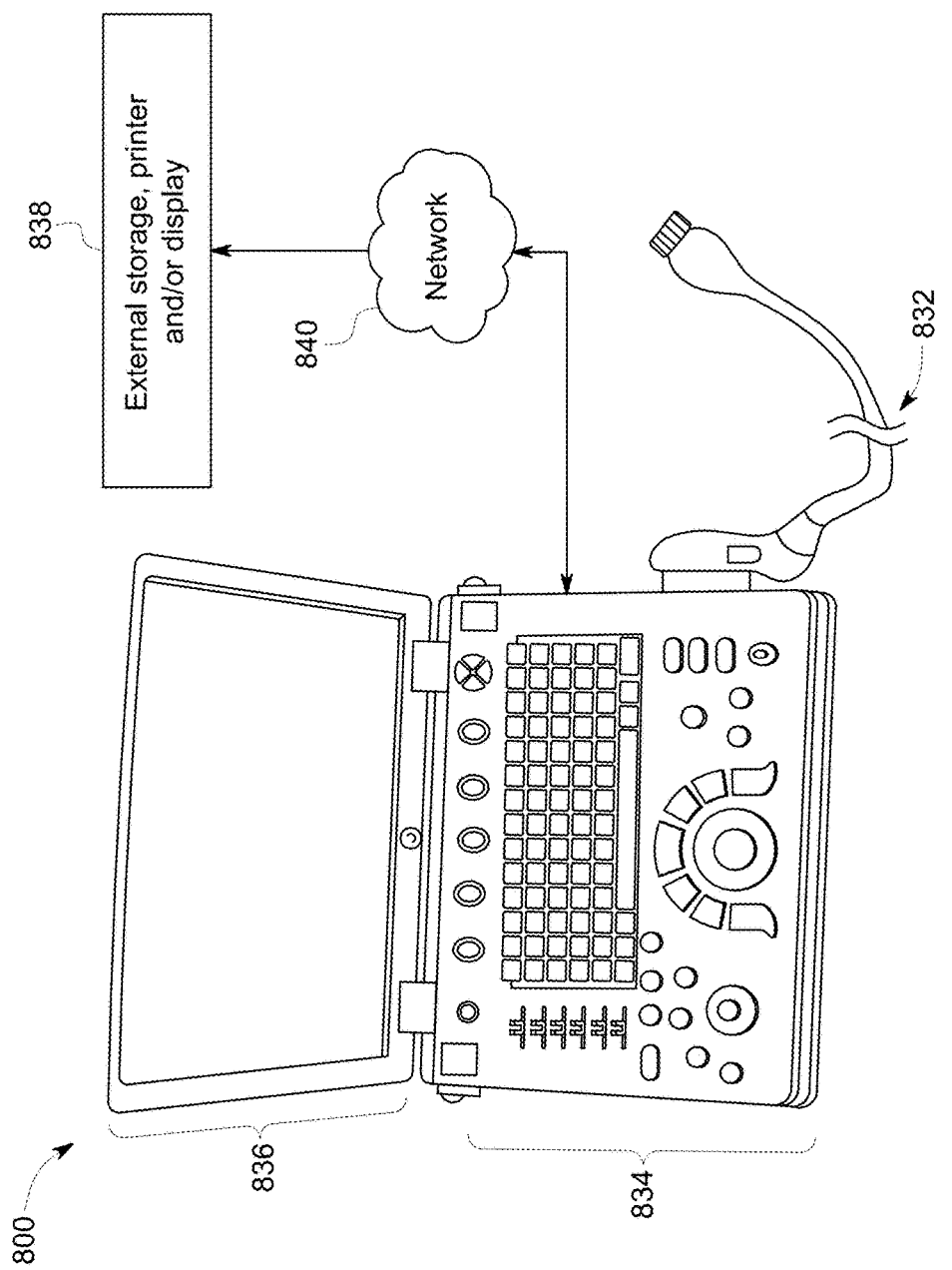
FIG. 8 illustrates a 3D capable miniaturized ultrasound system having a probe that may be configured to acquire 3D ultrasonic data or multi-plane ultrasonic data.
Figure 9:
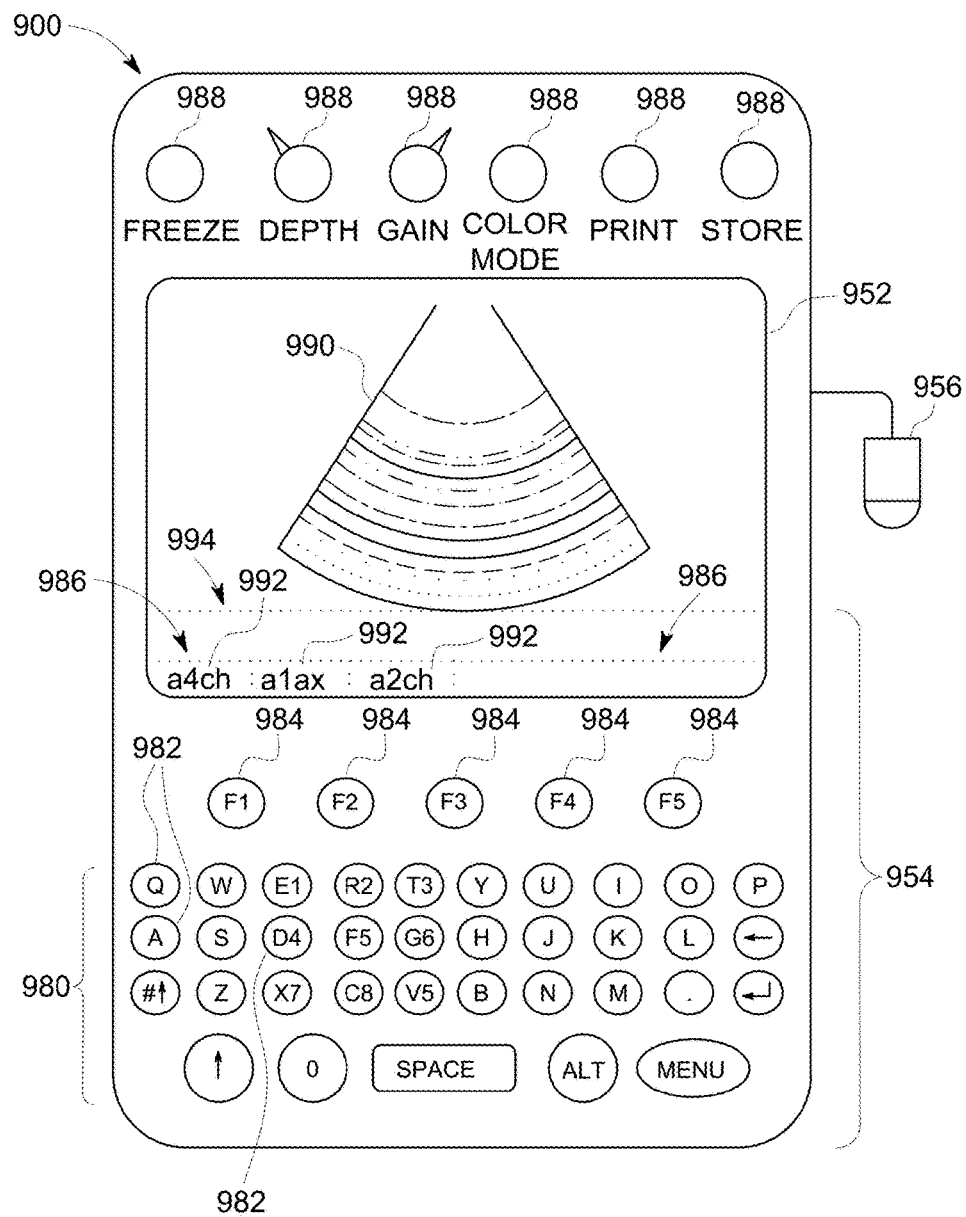
FIG. 9 illustrates a hand carried or pocket-sized ultrasound imaging system wherein the display and user interface form a single unit.
Figure 10:
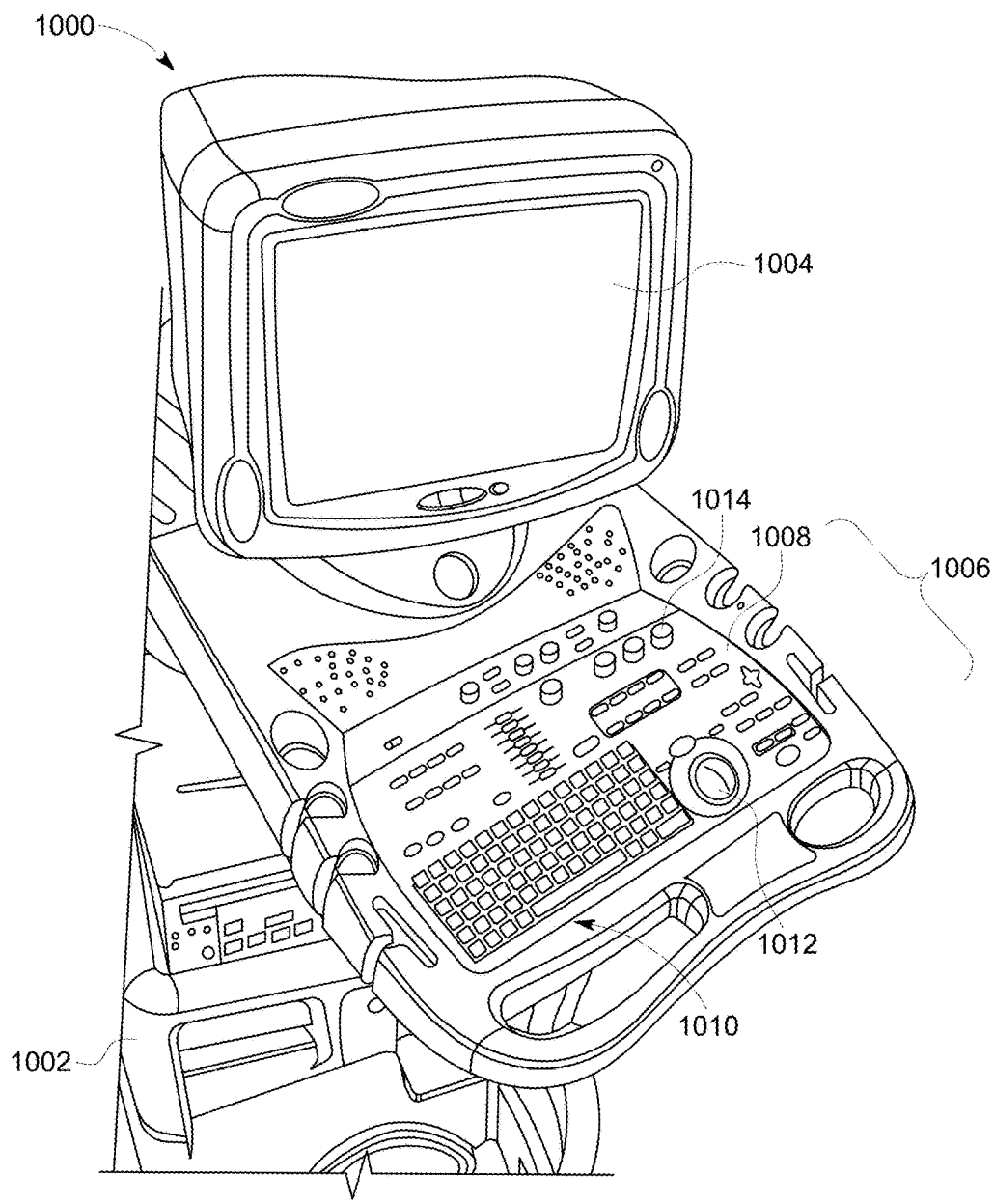
FIG. 10 illustrates an ultrasound imaging system provided on a movable base.

The ultrasound system 100 of FIG. 1 may be embodied in a small-sized system, such as laptop computer or pocket-sized system as well as in a larger console-type system. FIGS. 8 and 9 illustrate small-sized systems, while FIG. 10 illustrates a larger system.

FIG. 8 illustrates a 3D-capable miniaturized ultrasound system 800 having a probe 832 that may be configured to acquire 3D ultrasonic data or multi-plane ultrasonic data. For example, the probe 832 may have a 2D array of elements as discussed previously with respect to the probe. A user interface 834 (that may also include an integrated display 836) is provided to receive commands from an operator. As used herein, "miniaturized" means that the ultrasound system 800 is a handheld or hand-carried device or is configured to be carried in a person's hand, pocket, briefcase-sized case, or backpack. For example, the ultrasound system 800 may be a hand-carried device having a size of a typical laptop computer. The ultrasound system 800 is easily portable by the operator. The integrated display 836 (e.g., an internal display) is configured to display, for example, one or more medical images.

The ultrasonic data may be sent to an external device 838 via a wired or wireless network 840 (or direct connection, for example, via a serial or parallel cable or USB port). In some embodiments, the external device 838 may be a computer or a workstation having a display. Alternatively, the external device 838 may be a separate external display or a printer capable of receiving image data from the hand carried ultrasound system 800 and of displaying or printing images that may have greater resolution than the integrated display 836.

FIG. 9 illustrates a hand carried or pocket-sized ultrasound imaging system 900 wherein the display 952 and user interface 954 form a single unit. By way of example, the pocket-sized ultrasound imaging system 900 may be a pocket-sized or hand-sized ultrasound system approximately 2 inches wide, approximately 4 inches in length, and approximately 0.5 inches in depth and weighs less than 3 ounces. The pocket-sized ultrasound imaging system 900 generally includes the display 952, user interface 954, which may or may not include a keyboard-type interface and an input/output (I/O) port for connection to a scanning device, for example, an ultrasound probe 956. The display 952 may be, for example, a 320×320 pixel color LCD display (on which a medical image 990 may be displayed). A typewriter-like keyboard 980 of buttons 982 may optionally be included in the user interface 954.

Multi-function controls 984 may each be assigned functions in accordance with the mode of system operation (e.g., displaying different views). Therefore, each of the multi-function controls 984 may be configured to provide a plurality of different actions. One or more interface components, such as label display areas 986 associated with the multi-function controls 984 may be included as necessary on the display 952. The system 900 may also have additional keys and/or controls 988 for special purpose functions, which may include, but are not limited to "freeze," "depth control," "gain control," "color-mode," "print," and "store."

One or more of the label display areas 986 may include labels 992 to indicate the view being displayed or allow a user to select a different view of the imaged object to display. The selection of different views also may be provided through the associated multi-function control 984. The display 952 may also have one or more interface components corresponding to a textual display area 994 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 900 and the miniaturized ultrasound system 800 may provide the same scanning and processing functionality as the system 100.

FIG. 10 illustrates an ultrasound imaging system 1000 provided on a movable base 1002. The portable ultrasound imaging system 1000 may also be referred to as a cart-based system. A display 1004 and user interface 1006 are provided and it should be understood that the display 1004 may be separate or separable from the user interface 1006. The user interface 1006 may optionally be a touchscreen, allowing the operator to select options by touching displayed graphics, icons, and the like.

The user interface 1006 also includes control buttons 1008 that may be used to control the portable ultrasound imaging system 1000 as desired or needed, and/or as typically provided. The user interface 1006 provides multiple interface options that the user may physically manipulate to interact with ultrasound data and other data that may be displayed, as well as to input information and set and change scanning parameters and viewing angles, etc. For example, a keyboard 1010, trackball 1012 and/or multi-function controls 1014 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for measuring cardiac output, comprising:
generating an ultrasound image based on ultrasound imaging data of a patient acquired by an ultrasound probe;
automatically designating a region of interest (ROI) corresponding to a left ventricular outflow tract (LVOT) within the ultrasound image;
acquiring plural spectral data sets for corresponding spectral waveforms for corresponding plural candidate Doppler gates within the ROI based on Doppler data acquired by the ultrasound probe;
automatically identifying a select Doppler gate from the plural, candidate Doppler gates based on a characteristic of the spectral waveforms by comparing each of the spectral waveforms of each of the plural candidate Doppler gates with every other spectral waveform of every other candidate Doppler gate within the ROI, wherein a position of the identified select Doppler gate is configured to be displayed within the ROI within the ultrasound image; and
calculating a cardiac output of the patient based on the select Doppler gate.

2. The method of claim 1, wherein the Doppler data and the ultrasound imaging data are interleaved when acquired by the ultrasound probe.

3. The method of claim 1, further comprising analyzing the characteristic of the spectral waveforms with respect to a criteria threshold to identify the select Doppler gate.

4. The method of claim 1, further comprising:
calculating a velocity time integral (VTI) from an envelope of the corresponding spectral waveforms for the select Doppler gate, wherein the VTI and a cross sectional area (CSA) are used to calculate the cardiac output.

5. The method of claim 1, further comprising receiving a cross sectional area (CSA) of the LVOT based on at least one of a height, weight, or gender of the patient, wherein the cross sectional area of the LVOT is used to calculate the cardiac output.

6. The method of claim 1, further comprising determining when a first peak and a second peak occurs within a select spectrum waveform based on the spectral data set of the select Doppler gate;
calculating a heart rate based on when the first peak and the second peak occurs, wherein the heart rate is used to calculate the cardiac output.

7. The method of claim 1, wherein the characteristic corresponds to at least one of a duration, a direction, a peak velocity, power, or change in velocity of the spectral waveforms.

8. The method of claim 1, further comprising adjusting a position of the ROI based on a user selection.

9. The method of claim 1, further comprising selecting an alternative select Doppler gate from the plural candidate Doppler gates based on a user selection.

10. The method of claim 1, further comprising displaying indicia indicative of one or more characteristics of the plural candidate Doppler gates within the ROI.

11. An ultrasound imaging system for measuring a cardiac output comprising:
an ultrasound probe configured to acquire ultrasound imaging data and Doppler data of a patient;
a memory configured to store programmed instructions; and
one or more processors configured to execute the programmed instructions stored in the memory, wherein the one or more processors when executing the programmed instructions perform the following operations:
generate an ultrasound image based on the ultrasound imaging data;
designate a region of interest (ROI) corresponding to a left ventricular outflow tract (LVOT) within the ultrasound image;
acquire plural spectral data sets for corresponding spectral waveforms for corresponding plural candidate Doppler gates within the ROI based on the Doppler data;
identify a select Doppler gate from the plural candidate Doppler gates based on a characteristic of the spectral waveforms by comparing each of the spectral waveforms of each of the plural candidate Doppler gates with every other spectral waveform of every other candidate Doppler gate within the ROI, wherein a position of the identified select Doppler gate is configured to be displayed within the ROI within the ultrasound image; and
calculate a cardiac output of the patient based on the select Doppler gate.

12. The ultrasound imaging system of claim 11, wherein the Doppler data and the ultrasound imaging data are interleaved when acquired by the ultrasound probe.

13. The ultrasound imaging system of claim 11, wherein the one or more processors further analyze the characteristic of the select waveforms with respect to a criteria threshold to identify the select Doppler gate.

14. The ultrasound imaging system of claim 11, wherein the one or more processors further calculate a cross sectional area (CSA) of the left ventricular outflow tract (LVOT) of the ROI, wherein a velocity time integral (VTI) and the CSA are used to calculate the cardiac output.

15. The ultrasound imaging system of claim 11, wherein the one or more processors further determine when a first peak and a second peak occurs within a select spectrum waveform based on the spectral data set of the select Doppler gate, and calculate a heart rate based on when the first peak and the second peak occurs, wherein the heart rate is used by the one or more processors to calculate the cardiac output.

16. The ultrasound imaging system of claim 11, wherein the characteristic corresponds to at least one of a duration, a direction, a peak velocity, power, or change in velocity of the spectral waveforms.

17. The ultrasound imaging system of claim 11, further comprising a user interface, wherein the one or more processors further select an alternative select Doppler gate from the plural candidate Doppler gates based on a user selection from the user interface.

18. A tangible and non-transitory computer readable medium comprising one or more computer software modules configured to direct one or more processors to:

generate an ultrasound image based on ultrasound imaging data of a patient acquired by an ultrasound probe;

automatically designate a region of interest (ROI) corresponding to a left ventricular outflow tract (LVOT) within the ultrasound image;

acquire plural spectral data sets for corresponding spectral waveforms for corresponding plural candidate Doppler gates within the ROI based on Doppler data acquired by the ultrasound probe;

automatically identify a select Doppler gate from the plural candidate Doppler gates based on a characteristic of the spectral waveforms by comparing each of the spectral waveforms of each of the plural candidate Doppler gates with every other spectral waveform of every other candidate Doppler gate within the ROI; and calculate a cardiac output of the patient based on the select Doppler gate.

19. The tangible and non-transitory computer readable medium of claim 18, wherein the Doppler data and the ultrasound imaging data are interleaved when acquired by the ultrasound probe.

20. The tangible and non-transitory computer readable medium of claim 18, wherein the one or more processors are further directed to calculate a velocity time integral (VTI) from an envelope of the corresponding spectral waveforms for the select Doppler gate, where in the VTI and a cross sectional area (CSA) are used to calculate the cardiac output.

21. The method of claim 1, wherein a number of the acquired plural spectral data sets for the corresponding plural candidate Doppler gates is based on a size of the ROI.

22. The ultrasound imaging system of claim 11, wherein a number of the acquired plural spectral data sets for the corresponding plural candidate Doppler gates is based on a size of the ROI.

23. The tangible and non-transitory computer readable medium of claim 18, wherein a number of the acquired plural spectral data sets for the corresponding plural candidate Doppler gates is based on a size of the ROI.

* * * * *